United States Patent [19]

Christ et al.

[11] Patent Number: 5,494,946
[45] Date of Patent: * Feb. 27, 1996

[54] OPTICALLY CLEAR REINFORCED SILICONE ELASTOMERS OF HIGH OPTICAL REFRACTIVE INDEX AND IMPROVED MECHANICAL PROPERTIES FOR USE IN INTRAOCULAR LENSES

[75] Inventors: Richard Christ, Orange; Brian A. Nash, Carpinteria; Del J. Petraitis, Goleta, all of Calif.

[73] Assignee: Allergan, Inc., Irvine, Calif.

[*] Notice: The portion of the term of this patent subsequent to Aug. 17, 2010, has been disclaimed.

[21] Appl. No.: 315,279

[22] Filed: Sep. 29, 1994

Related U.S. Application Data

[62] Division of Ser. No. 86,763, Jun. 30, 1993, Pat. No. 5,376,694, which is a division of Ser. No. 870,799, Apr. 17, 1992, Pat. No. 5,236,970, which is a continuation of Ser. No. 562,452, Aug. 1, 1990, abandoned, which is a continuation of Ser. No. 292,212, Dec. 29, 1988, abandoned, which is a continuation of Ser. No. 11,021, Feb. 5, 1987, abandoned.

[51] Int. Cl.$^6$ .................................................. C08L 83/05
[52] U.S. Cl. .................... 523/113; 524/588; 524/862
[58] Field of Search ........................ 523/113; 524/588, 524/862

[56] References Cited

U.S. PATENT DOCUMENTS

| | | | |
|---|---|---|---|
| 3,284,406 | 11/1966 | Nelson | 528/31 |
| 3,341,490 | 9/1967 | Burdick et al. | 523/212 |
| 3,436,366 | 4/1969 | Modic | 524/862 |
| 3,457,214 | 7/1969 | Modic | 524/863 |
| 3,996,187 | 12/1976 | Travnicek | 523/107 |
| 3,996,189 | 12/1976 | Travnieck | 523/107 |
| 4,380,643 | 4/1983 | Yoshida et al. | 548/260 |
| 4,418,165 | 11/1987 | Polmanteer et al. | 523/117 |
| 4,535,141 | 8/1985 | Kroupa | 528/15 |
| 4,573,998 | 4/1986 | Mazzocco et al. | 623/6 |
| 4,615,702 | 10/1986 | Kozioi | 623/6 |
| 4,647,282 | 3/1987 | Fedofov et al. | 627/4 |
| 4,868,251 | 9/1989 | Reich | 525/479 |
| 5,236,970 | 8/1993 | Christ et al. | 523/117 |
| 5,376,694 | 12/1994 | Christ | 523/113 |

FOREIGN PATENT DOCUMENTS

| | | |
|---|---|---|
| 110537 | 6/1984 | European Pat. Off. |
| 2114315 | 8/1983 | United Kingdom |

OTHER PUBLICATIONS

Noll, Walter, Chemistry and Technology of Silicones, Academic Press, New York, 1969, p. 3.

Primary Examiner—Ralph H. Dean
Attorney, Agent, or Firm—Frank J. Uxa

[57] ABSTRACT

Optically clear, reinforced cross-linked silicone elastomers of the invention contain 12 to 18 mol percent of aryl substituted siloxane units of the formula $R_4R_5$-SiO, end blockers containing silioxane units of the formula $R_1R_2R_3$-$S:O_{0.5}$, and dialkyl siloxane units of the formula $R_6R_7$-SiO. $R_1$ and $_2$ are alkyl, aryl or substituted alkyl or substituted aryl groups, and $R_3$ is an alkenyl group. $R_4$ and $R_5$ are phenyl or mono lower alkyl substituted phenyl groups. $R_6$ and $R_7$ are methyl or ethyl groups. The polymer has a degree of polymerization between 100 to 2000, and preferably approximately 250. The polymer also contains trimethyl silyl treated silica as a reinforcer in the weight ration of approximately 15 to 45 parts of reinforcer to 100 parts of the polymer. After cross-linking, the polymer has properties of an optical refractive index which is at least 1.44, a type A durometer hardness of at least 35, tensile strength of at least 500 psi and tear strength of at least 20 pli. The foregoing properties render the cross-linked polymer especially suitable for forming the bodies of intraocular lenses.

19 Claims, No Drawings

OPTICALLY CLEAR REINFORCED SILICONE ELASTOMERS OF HIGH OPTICAL REFRACTIVE INDEX AND IMPROVED MECHANICAL PROPERTIES FOR USE IN INTRAOCULAR LENSES

This application is a division of application Ser. No. 08/086,763, filed Jun. 30, 1993, now U.S. Pat. No. 5,376,694, which is a division of application Ser. No. 07/870,799, filed Apr. 17, 1992, now abandoned, U.S. Pat. No. 5,236,970, now abandoned, which is a continuation of application Ser. No. 07/562,452, filed Aug. 1, 1990, which is a continuation of application Ser. No. 07/292,212, filed Dec. 29, 1988, now abandoned, which is a continuation of application Ser. No. 07/011,021, filed Feb. 5, 1987, now abandoned.

Intraocular lenses made from silicone polymeric materials are usually deformable, so that for implantation a smaller incision needs to be surgically cut in the eye than for the implantation of "hard" intraocular lenses. In this respect, the size and mechanical characteristics of the silicone polymeric intraocular lenses play an important role. As it will be well understood by those skilled in the art, for successful implantation the lens must have sufficient structural integrity, elasticity and small enough size to permit the folding for insertion through a small incision. After insertion, the lens must, of course, regain its original molded shape.

It will be further understood by those skilled in the art that the thinner is the lens, the easier is the surgical insertion procedure. On the other hand, in order to function as an intraocular lens, the lens materials must have sufficient optical refractory power. Consequently, the higher is the optical refractive index of the silicone material, the thinner can be the lens to obtain the same optical refractory power.

Some silicone polymeric materials described in the prior art contain a silica reinforcer finely distributed in the polymeric silicone resin. Usually such reinforcement of the silicone polymeric material with silica is necessary for the polymeric material to attain adequate structural strength to be used as a foldable intraocular lens. Such silica reinforced polymeric silicone resins suitable for use as soft contact or intraocular lenses are described in U.S. Pat. Nos. 3,996,187; 4,615,702; 3,996,189. Additional disclosures relating to polymeric silicone materials or silica reinforcers, which comprise the background of the present invention can be found in U.S. Pat. Nos. 3,341,490; 3,284,406; 3,457,214; and in European Patent Application No. 0110537 filed on Oct. 18, 1983.

Additional disclosures relating to intraocular lenses can be found in U.S. Pat. No. 4,573,998, published UK Patent Application GB 2114315, and in co-pending application for U.S. Pat. Ser. No. 946,703, filed on Dec. 24, 1986, by *Reich et al.*, now abandoned. The latter U.S. patent application is assigned to one of the co-assignees of the present invention.

The prior art intraocular lenses made of silica reinforced silicone copoymers still do not fully satisfy the need for high enough optical refractory power to permit sufficiently thin lens size which in turn would make it possible to surgically implant the lens through a desirably small incision in the eye. In other words, there is still need in the art for reinforced silicone polymeric materials which have sufficiently high optical clarity, refractive index, durometer hardness, tensile strength and related mechanical properties to permit construction of thin foldable intraocular lenses. The present invention satisfies this need.

SUMMARY OF THE INVENTION

It is an object of the present invention to provide optically clear reinforced silicone polymeric materials of a refractive index of at least 1.44 coupled with sufficient durometer hardness, tensile strength and other mechanical properties to permit forming of thin intraocular lenses through final cross-linking of the polymeric material into desired lens shapes.

It is another object of the present invention to provide a thin intraocular lens body from a reinforced silicone polymeric material, wherein the lens body has an optical refractive index of at least 1.44 and sufficient mechanical properties to permit implantation through a small incision in the eye.

The foregoing objects and advantages are attained by an optically clear, reinforced cross-linked silicone elastomer which includes a polymer containing 12 to 18 mol percent of aryl substituted siloxane units of the formula $R_4R_5$-SiO. In the formula $R_4$ and $R_5$ are identical with one another or are different from one another and represent phenyl, or mono- lower alkyl substituted phenyl groups, or di- lower alkyl substituted phenyl groups. Preferably both $R_4$ and $R_5$ are phenyl.

The polymer has end blockers containing siloxane units of the formula $R_1R_2R_3$-Si-$O_{0.5}$ wherein $R_1$ and $R_2$ are alkyl, aryl or substituted alkyl or substituted aryl groups, and $R_1$ and $R_2$ may be identical or different from one another. The $R_3$ group of the end blocking siloxane units is an alkenyl group. Preferably, the end blocker is a dimethylvinyl siloxane unit.

The balance of the polymer consists of dialkyl siloxane units of the formula $R_6R_7$-SiO wherein $R_6$ and $R_7$ are identical with one another or are different from one another and are methyl or ethyl groups, and the polymer has a degree of polymerization approximately between 100 to 2000. Preferably, the $R_6$ and $R_7$ units are both methyl, and the degree of polymerization is approximately 250.

A trimethyl silyl treated silica reinforcer is finely dispersed in the polymer, in a weight ratio of approximately 15 to 45 parts of the reinforcer to 100 parts of the polymer. Preferably, there is approximately 27 parts of reinforcer to 100 parts of the copolymer.

The polymer when cured by cross-linking in a mold forms the body of an intraocular lens of the invention, and has the properties of an optical refractive index which is at least 1.44, a type A durometer hardness value of at least 35, a tensile strength of at least 500 psi, and a tear strength of at least 20 pli.

Further objects and advantages of the present invention will become readily apparent from the ensuing description wherein the specific embodiments are described as follows.

DESCRIPTION OF THE SPECIFIC EMBODIMENTS

Reinforced elastomeric polysiloxane copolymer compositions are provided in accordance with the present invention, which after appropriate curing by cross-linking, are eminently suitable to serve as the body of foldable "soft" intraocular lenses capable of implantation through a small incision in the eye.

More particularly, the reinforced elastomeric composition of the present invention has the chemical composition of a cross-linked copolymer including approximately 12 to 18 mol per cent of aryl substituted siloxane units of the formula $R_4R_5$-SiO where the aryl substituents ($R_4$ and $R_5$ groups) can be phenyl groups, mono- lower alkyl substituted phenyl groups, or di- lower alkyl substituted phenyl groups, and can be identical with one another or different from one another. Preferably, both aryl groups are simple phenyl, and the resulting diphenyl siloxane unit is present in the copolymer in a ratio of approximately 14 to 16 mol per cent. In the hereinafter described specific example, the diphenyl siloxane unit content of the copolymer is approximately 15 mol per cent.

It is noted in connection with the diaryl, preferably simple diphenyl substituted siloxane units, that the presence of the aryl groups tends to increase the optical refractive index of the copolymer.

The copolymer is end blocked with trisubstituted (monofunctional) siloxane units, an important feature of which is that at least one substituent of the end blocking group contains an olefenic bond. Thus, the general formula of the end blocking group incorporated in the copolymer of the invention is $R_1R_2R_3\text{-}S\text{:}O_{0.5}$ where the nature of the $R_1$ and $R_2$ is not critical, and they may be, for example, alkyl, aryl, or substituted alkyl or substituted aryl groups. $R_1$ and $R_2$ may be identical to one another, and may also be different from one another. The nature of the $R_3$ group is important in that $R_3$ contains an olefenic bond. Thus, $R_3$ is an alkenyl group, preferably a vinyl group. In the preferred embodiment of the invention the end blocking group is a dimethyl, vinyl siloxane unit. The role of the olefenic (vinyl) group, is to enable curing or cross-linking of the polymer as well as covalently linking, in accordance with another feature, certain ultraviolet light absorbing compounds to the cross-linked copolymer matrix of an intraocular lens made in accordance with the invention.

The balance of the siloxane building blocks of the copolymer are dialkyl siloxane units wherein the two alkyl substituents are either ethyl or methyl. In other words, the general formula of the balance of the siloxane building blocks of the copolymer is $R_6R_7\text{-}SiO$ where the $R_6$ and $R_7$ groups are methyl or ethyl and the two groups are either identical with one another, or are different from one another. Preferably in the practice of the present invention both $R_6$ and $R_7$ groups are methyl.

In accordance with the present invention the copolymer having the above-described components has a degree of polymerization (dp) of approximately 100 to 2000, although a degree of polymerization of approximately 250 is preferred particularly when the $R_4$ and $R_5$ groups are phenyl and the $R_6$ and $R_7$ groups are methyl.

Except to the extent that novel features are emphasized below, the preparation of the copolymer having the above described components can be performed in accordance with processes known in the art, from starting materials which are either commercially available or can be made in accordance with well known state-of-the-art processes.

Thus, in accordance with standard practice in the art, readily available cyclic oligomers of the components and suitable state-of-the-art precursors of the end blocking groups are reacted in the presence of a suitable catalyst to achieve polymerization to the desired degree. The cyclic oligomer starting materials are best exemplified by reference to the specific example of the most preferred embodiment of the copolymer of the invention. Specifically, a mixture of octaphenylcyclo-tetrasiloxane, octamethylcyclo-tetrasiloxane and 1,2 divinyltetramethyldisiloxane are reacted in the presence of a polymerization catalyst to achieve a degree of polymerization which is approximately 250 for the preferred embodiment.

It should be specifically understood in connection with the preparation of the copolymer that after the proper copolymer composition is selected, the selection of suitable starting materials for the polymerization is within the skill of the ordinary artisan. Similarly, the polymerization can be conducted by using state of the art catalyst; the well known N-catalysts and K-catalyst are particularly of choice in this regard. As is known in the art, the K-catalyst used for polysiloxane formation comprise potassium hydroxide, whereas the N-catalyst comprise tetramethylammonium hydroxide.

It is an important aspect of the process for preparing the copolymer of the present invention that the degree of polymerization is monitored by monitoring the viscosity of the reaction mixture. Moreover, the optical refractive index of the reaction mixture is also monitored, and the reaction is not considered completed, nor giving acceptable product unless the reaction mixture has a viscosity within a desired range and an optical refractive index of at least 1.44. The desired viscosity range depends on the nature and composition of the copolymer; for the preferred copolymer having dimethylvinylsiloxane end blockers, approximately 15 mol per cent diphenyl siloxane building blocks with the balance being dimethylsiloxane, and a degree of polymerization of approximately 250, the desired viscosity range of the reaction produce is approximately 2000 to 2800 centipoise (cp). In this connection it is noted that whereas the aryl content of the copolymer greatly influences the refractive index, the degree of polymerization does not. The degree of polymerization, on the other hand, greatly influences the viscosity of the polymer.

After the desired level of polymerization and refractive index is achieved, the catalyst is inactivated, neutralized, or removed and the reaction product is carefully filtered, for example on a filter press, to remove any unreacted solid starting materials or other solid impurities.

After filtration, volatile materials are carefully removed from the copolymer by repeated exposure to vacuum, preferably while the copolymer is in a thin film form. The careful removal of volatiles, commonly termed "stripping", is considered important for the purpose of obtaining materials suitable for use as intraocular lens. The "stripping" is preferably conducted in a state-of-the-art "wipe film evaporator" using large "wipe films" and the process is monitored by gas column chromatography of the removed volatiles. As it will be readily appreciated by those skilled in the art, the removed "volatiles" are residues of starting materials, cyclic and linear oligosiloxanes and the like.

Moreover, because in virtually every polymerization the molecular weight, or degree of polymerization of the resulting polymeric products follow a substantially bell shaped curve, the crude reaction product copolymer of the present invention also contains products having substantially lesser degree of polymerization, than for example the desired dp of 250 for the preferred embodiment. In this regard it should be understood that a dp of 250 of the preferred embodiment is to be construed as such dp numbers are normally construed in the art of polysiloxane chemistry. A dip of 250 thus means that the average dp of the polymeric product is approximately 250.

Stripping of the copolymeric product is repeated several times, preferably three times. This process removes a significant amount of the lower dp copolymers; usually approximately 12 percent by weight of the reaction product is removed by "stripping".

It is considered important in the practice of the present invention to monitor viscosity and refractive index at the end of the process of removing volatiles. The refractive index of the copolymer should be at least 1.44. As it was noted above, the desired viscosity depends on the precise nature of the copolymer, for the preferred embodiment the viscosity of the "stripped" copolymer should be approximately 4100 to 5300 cp.

The elastomeric composition of the present invention contains a trimethylsilyl treated silica reinforcer finely dispersed in the copolymer. Blending trimethylsilyl treated "fume silica" into a polysiloxane copolymer for the purpose of improving the mechanical properties of the resulting composition per se, is not new in the art. Nevertheless, the composition of the present invention is considered novel and highly unobvious because of the hitherto unattained higher desirable optical and mechanical properties of the reinforced composition.

In accordance with the invention, the fume silica reinforcer is used in a ratio of approximately 15 to 45 parts by weight of the reinforcer to 100 parts of the copolymer. Fume silica itself is commercially available. Processes for trimethylsilylating the surface of fume silica for the purpose of rendering the silica surface hydrophobic and compatible with polysiloxane polymers are also known and within the skill of the ordinary artisan. U.S. Pat. Nos. 3,341,490 and particularly 3,036,985, refer to and describe such processes for trimethylsilylating fume silica, and the specifications of these two patents are expressly incorporated herein by reference.

In accordance with the present invention the fume silica reinforcer used to the composition has a surface area of approximately 100 to 450 meter$^2$/gram. For the preferred embodiment of the composition the fume silica has a surface area of approximately 200 meter$^2$/gram, is present in a weight ratio of approximately 27 parts to 100 parts of the copolymer, and is preferably trimethylsilylated with hexamethyldisilazane substantially in the same step where the copolymer is intimately mixed with the silica. The intimate mixing is preferably aided by treating the mixture on a roll mill or like device. After intimate mixing, volatiles, such as unreacted silylating agent, gaseous by-products and water are removed from the mixture by heat and vacuum.

The intimate mixture of the trimethylsilylated fume silica with the copolymer is commonly termed "base" in the art. For the purpose of making materials suitable for intraocular lens, the base is dispersed in a suitable inert solvent, such as trichlorotrifluoroethane (FREON) and the dispersion is filtered to remove any solid impurities. Thereafter, the solvent is removed by gentle heat and vacuum.

The resulting, volatile free uncured (not yet cross-linked) and optically clear reinforced silicone elastomer base, has in accordance with the present invention, an optical refractive index of at least 1.44 and a viscosity in such a range which permits intimate mixing of the base with suitable catalyst and cross linking agents, and subsequent manipulation for forming, preferably by molding, into intraocular lenses. The acceptable viscosity range for this purpose is approximately 35,000 to 80,000 cp. For the preferred embodiment of the invention, the refractive index of the uncured base is approximately 1.462±0.003 and the viscosity is in the range of 35,000 to 70,000 cp.

It is an important feature of the present invention that the uncured ease has the inherent characteristics of providing, after suitable curing by cross-linking, physical properties which are highly advantageous for a soft intraocular lens. Thus, after the hereinafter described curing or cross-linking steps, the properties of the resulting cross-linked elastomer include in accordance with the present invention the following:

an optical refractive index which is at least 1.44;

a Shore A durometer hardness value of at least 35;

a tensile strength of at least 500 psi;

a 150 percent minimum elongation (without damage), and a tear strength of at least 20 pounds per lineal inch (pli).

The above listed properties can be measured in accordance with state-of-the-art technology and instruments in accordance with the respective requirements of standard ASTM test methods. More particularly, the durometer test is performed as ASTM D2240, the tensile and elongation tests as ASTM D412 and the tear strength test as ASTM D624 Die B.

Preferably, the optical refractive index of the cross-linked elastomer obtainable from the base is approximately 1.462, the durometer hardness is approximately between 38 to 40, the tensile strength is approximately between 700 to 750 psi, and the tear strength is approximately 40 pli. In this regard it is noted that cross-linking tends to slightly increase the optical refractive index as compared to the uncured base.

Preparation of the uncured base for cross-linking is accomplished as follows. The base is filtered once more, preferably through a 325 mesh screen to remove any remaining solid impurities. Thereafter, in accordance with standard practice in the art, the base is divided into two aliquots which preferably are of equal weight. The aliquots are commonly termed "Part A" and "Part B", or first and second aliquot parts.

As is known in the art, cross-linking is accomplished by utilizing in a platinum catalyzed reaction the terminal silicon bonded olfinic (vinyl) groups of the base, and silicon bonded hydrogen groups. The silicon bonded olefinic (vinyl) groups are present both in the first and second aliquots of the base.

Silicon bonded hydrogen groups are added in the practice of the present invention to the second aliquot (Part B) in the form of suitable cross-linking agents. The cross-linking agents per se are known in the art, and may be made in accordance with the teachings of U.S. Pat. No. 3,436,366, the specification of which is incorporated herein by reference.

Whereas a number of cross-linking agents are suitable for the practice of the invention and can be selected by those skilled in the art, the liquid organohydrogen polysiloxane cross-linkers shown in Column 2 of the above-noted U.S. Pat. No. 3,436,366, and having the formula $(R)_a(H)_bSiO_{4-a-b/2}$ wherein R is simple lower alkyl and a ranges from 1.00 to 2.10 and b ranges from 0.1 to 1.0, are eminently suitable. Particularly suitable is the liquid organohydrogen polysiloxane cross-linker of the above-referenced U.S. Pat. No. 3,436,366, having the formula $R_2HSiO_{1/2}$, and the liquid cross-linker described in Column 4 lines 3–14 of said patent reference wherein the R groups are primarily or predominantly methyl.

The platinum catalyst can also be selected within the skill of the ordinary artisan, primarily from organo platinum compounds, for example in accordance with the specifications of U.S. Pat. Nos. 2,823,218 and 3,159,601, which are expressly incorporated herein by reference. The platinum catalyst is added to the first aliquot (Part A).

It is important in accordance with the invention that after mixing of the aliquots (Parts A and Parts B), the cross-linking should not proceed too rapidly at room temperature, thereby allowing at least two, preferably approximately six hours for work time with the mixed aliquots. For this reason, a suitable cross-linking inhibitor, such as 1,2,3,4 tetramethyl- 1,2,3,4-tetravinyl cyclotetrasiloxane, is also added to the second aliquot (Part B).

Although the precise amounts can be adjusted within the skill of ordinary artisan, the organo platinum catalyst is added to the first aliquot in 12 part per million (12 ppm) by weight. The cross-linker is added to the second aliquot in the range of approximately 1 to 6 parts per hundred (1–6 pph) by weight. The above specified inhibitor is also added to the second aliquot in the range of 0.01 to 0.2 parts per hundred by weight.

It has been found in accordance with the present invention that best results, in terms of desired curing times, are obtained when the amount of inhibitor used in the second aliquot is adjusted on small samples of each batch. The adjustment within the above-noted ranges serves to provide approximately 6 hours of work time at room temperature. In other words, the material should not cure significantly at room temperature within six hours. Before curing or cross-linking, the first and second aliquots are intimately mixed, preferably in equal amounts.

In addition to the above-described cross-linker and inhibitor, an ultraviolet ray absorbing material is also optionally mixed into the second aliquot in accordance with the teachings of co-pending application for U.S. Pat. Ser. No. 946, 703, filed on Dec. 24, 1986, by *Reich et al.,* and titled ULTRAVIOLET LIGHT ABSORBING SILICONE COMPOSITIONS.

The ultraviolet ray absorbing material, which in accordance with teachings of the above-noted patent application is a vinyl functional 2-hydroxybenzophenone, or a vinyl functional benzotriazole is covalently linked to the copolymer of the composition during the cross linking step. Preferably, the ultraviolet absorbing material is 2(2'-hydroxy-3'-t-butyl-5'-vinyl-phenyl)- 5-chloro-2H-benzotriazole, and is added in an amount of approximately 0.5 weight percent to the second aliquot. Consequently, in the final cured elastomer, the above-named u. v. absorbent is present in approximately 0.25 per cent (by weight).

Although the chemical reactions involved in the cross-linking are well known in the art, they are summarized here for the sake of completeness as involving the formation of ethylenic ($CH_2$—$CH_2$) bridges linking one copolymer chain to a polysiloxane cross linking molecule. The polysiloxane cross linker molecule, in turn, is again linked through an ethylenic bridge to a second copolymer chain. In essence, the chemical reaction involves saturation of a vinyl (or other unsaturated) groups of an end blocker with the hydrogen derived from an at least difunctional organohydrogen polysiloxane and formation of a carbon to silicon bond. This reaction is catalyzed by the platinum catalyst.

The vinyl functional u. v. absorbant reacts with the organohydrogen polysiloxane cross-linking agent in essentially the same way as the vinyl group of the copolymer, and forms a carbon to silicon bond which covalently links the u. v. absorber to the copolymer network.

Formation of intraocular lens bodies from the elastomeric compositions of the present invention may be accomplished by liquid injection molding or by cast or compression molding of the intimately mixed first and second aliquots. Although these processes are well known in the art, they are briefly summarized by description of the following examples.

In the liquid injection molding process the mixed aliquots are injected into a hot mold kept at approximately 120° to 150° C. The cross-linking or curing process is then complete in approximately five minutes.

In the cast or compression molding process, the mixed aliquots are placed into appropriate molds, and the molds are thereafter positioned in an oven heated to approximately 150° C. Under these conditions the cure is complete in approximately 15 to 30 minutes. The cast molding process can also be completed at room temperature in significantly longer time periods.

The intraocular lenses made in accordance with the present invention have the above-described advantagous optical and mechanical properties. The unusually high optical refractive index of 1.44 or greater, permits the fabrication of lenses which are at their apex only approximately 1.1 to 1.15 mm thick. This is a significant advance over prior art intraocular lenses which, being made of materials having lower refractive indices, typically are 1.42 mm thick at their apex.

An additional advantage of the intraocular lenses made in accordance with the invention is that they do not absorb energy at 1064 nm, thereby permitting follow-up LASER surgery in the eye after implantation of the lens.

Several modifications of the invention may become readily apparent to those skilled in the art in light of the foregoing disclosure. Therefore the scope of the present invention should be interpreted solely from the following claims. Further particulars of the preferred embodiment of the invention are described in the following description of an example of making the elastomeric compositions of the invention.

SPECIFIC EXAMPLE

Preparation of Crude Copolymer

In a 50 gallon reactor (Baker Perkins) mix octaphenylcyclotetrasiloxane (phenyl cyclics) (44.550 kg), octamethylcyclotetrasiloxane (dimethylcyclics) (93.462 kg) and 1,2-divinyltetramethyldisiloxane (1.116 kg) and heat under agitation and a nitrogen gas blanket to 100° C. When the temperature reaches 100° C. add 0.18 per cent (by weight) N-catalyst (about 250 g). Continue heating and stirring and monitor viscosity of samples taken from the reaction mixture. If after 45 minutes there is no change in viscosity, add 0.18 per cent more N-Catalyst (about 75 g). After viscosity change has been observed and the phenyl cyclics have dissolved continue heating and stirring for 3 hours. Then neutralize or destroy the catalyst, for example by bubbling $CO_2$ into the mixture, or heating to 150° C. Viscosity of the cooled reaction mixture should be between 2000 to 2800 cp, the refractive index should be between 1.459 to 1.465.

Purification of Copolymer

Filter the cooled reaction mixture on a filter press with a pressure of about 40 psi on five or more filter plates using Zeta Plus filter paper, catalog #A1311-10A. Strip the filtered copolymer at least three times on a "wipe film evaporator". Monitor the process of stripping by gc, taking samples of 1 g of the volatiles and dissolving the same in 3 g of hexane. Continue stripping until gc indicates adequate devolatilization. Viscosity of stripped copolymer should be between 4100 to 5300 cp, the refractive index should be between 1.459 to 1.465.

Formulation of Base Including Silica Reinforcer

In a 50 gallon mixer mix the stripped polymer (75 kg) with hexamethyldisilazane (3.6 kg). Add MS-7 silica (30 kg, surface area 200 $m^2/g$) in increments, and with last silica load add distilled water (1.2 kg), mix well. Thereafter mill mixture twice on three roll mill, and return mixture to 50 gallon mixer. Heat mixer to reach internal temperature of 150° to 200° C. After 30 minutes of heating and stirring at above temperature, apply vacuum and continue heating for 2.5 hours while the mixer reactor is under vacuum. Cool mixture under vacuum. After cooling add more stripped polymer (36.11 kg) as a "cut-back" and mix well. Let a small sample of base settle (unstirred) for about 30 minutes and check viscosity at 25° C. with Brookfield viscometer, viscosity should be between 35,00 to 70,000 cp.

Purification of Base

Disperse the base in trichlorotrifluoraethane (FREON) in a ratio of about 2 gallons of base to 1 gallon of FREON, and add about 0.5 gallon of diatomaceous earth to the dispersion for each 2 gallons of base. Filter the dispersion on a filter press using Zeta Plus filter paper, catalog #A1311-10A. Pressure during filtration should be kept at about 30 psi and should not exceed that value. Clear filrate is required. Place the collected clear filtrate in a reactor, and agitate under nitrogen purge. Apply vacuum gradually while purging slowly with nitrogen. Heat slowly to 110° C. and continue heating under vacuum. Take samples for weight loss test. Continue heating under vacuum until weight loss on samples taken indicates no more than 0.5 per cent loss. Thereafter cool to obtain stripped base.

Preparation of Aliquots (Parts A and B) Ready for Cross-Linking

Screen stripped base through 325 mesh steel wire screen under pressure. Divide the batch into two equal parts, Part A and Part B. Mix into Part A the organoplatinum catalyst to provide 12 parts per million by weight. Take small samples from Part B and mix in the cross-linker (liquid organohydrogen polysiloxane having the structure $R_2HSiO_{1/2}$ with the R groups being predominantly methyl). Optimize the cross-linker level, so as to obtain a Shore durometer hardness of approximately 35 (ASTM D2240) in the cross-linked product. Thereafter, gradually add increasing amounts of the inhibitor (1,2,3,4 tetramethyl-1,2,3,4-tetravinyl cyclotetrasiloxane) to Part B and test mixed samples of Parts A and B to obtain a working time of about 6 hours at room temperature. Depending on the above-noted sample test results, the cross-linker is added to Part B to provide 1–6 parts per hundred by weight, and the inhibitor is added to Part B to provide 0.01 to 0.2 parts per hundred by weight.

Optionally, intimately mix in the u. v. light absorbant 2(2'-hydroxy-3'-t-butyl-5'-vinyl-phenyl)-5-chloro-2H-benzotriazole in an amount which corresponds to approximately 0.5 per cent by weight in Part B.

Screen Part A and Part B separately from one another on 325 mesh screen to remove any solid contaminants. For cross-linking or curing to obtain intraocular lenses proceed in accordance with procedures required for liquid injection molding, or cast molding.

What is claimed is:

1. An intraocular lens suitable for surgical implantation into a human eye comprising an appropriately sized lens body capable of being folded, and made of an optically clear elastomeric material comprising:

a cross-linked silicone polymer containing approximately 12 to 18 mol percent of aryl siloxane units; and reinforcer component present in an amount effective to reinforce said polymer, said lens body having physical properties sufficient to enable said lens body to be placed in a folded shape for insertion into a human eye and to unfold into an unfolded shape after said insertion, said physical properties including:

an optical refractive index of at least 1.44;

a shore Type A durometer value of at least 35;

a tensile strength of at least 500 to about 750 psi; and a tear strength of at least 20 pli.

2. The intraocular lens of claim 1 wherein said cross-linked silicone polymer includes alkylsiloxane units.

3. The intraocular lens of claim 1 wherein said aryl siloxane units have the formula $R_4 R_5$-SiO wherein $R_4$ and $R_5$ are independently selected from phenyl, mono-alkyl substituted phenyl or di-alkyl substituted phenyl.

4. The intraocular lens of claim 1 wherein said aryl siloxane units are diphenyl siloxane units.

5. The intraocular lens of claim 2 wherein said alkyl siloxane units have the formula $R_6 R_7$-SiO wherein $R_6$ and $R_7$ are independently selected from methyl or ethyl.

6. The intraocular lens of claim 1 wherein said polymer includes end blockers containing siloxane units of the formula $R_1 R_2 R_3$-SiO$_{0.5}$ wherein $R_1$ and $R_2$ are independently selected from alkyl, aryl, substituted alkyl and substituted aryl, and $R_3$ is alkenyl.

7. The intraocular lens of claim 1 wherein said lens body has an optical refractive index of at least 1.459.

8. The intraocular lens of claim 1 wherein said lens body has physical properties sufficient to enable said lens to be placed in a folded shape for insertion into a human eye through a small incision.

9. The intraocular lens of claim 6 wherein $R^1$ and $R_2$ are methyl, and $R_3$ is vinyl, and said reinforcer component is silica.

10. An intraocular lens suitable for surgical implantation into a human eye comprising an appropriately sized lens body capable of being folded, and made of an optically clear material comprising:

a cross-linked silicone polymer containing approximately 12 to 18 mol percent of aryl siloxane units; and silica reinforcer present in an amount effective to reinforce said polymer, said lens body having an optical refractive index of at least 1.44 and other physical properties, including a combination of hardness, tensile strength, elongation and tear strength, sufficient to enable said lens body to be placed in a folded shape for insertion into a human eye and to unfold into an unfolded shape after said insertion, said lens body having a 150 percent minimum elongation.

11. The intraocular lens of claim 10 wherein said silicone polymer includes alkyl siloxane units.

12. The intraocular lens of claim 10 wherein said aryl siloxane units have the formula $R_4 R_5$-SiO wherein $R_4$ and $R_5$ are independently selected from phenyl, mono-alkyl substituted phenyl or di-alkyl substituted phenyl.

13. The intraocular lens of claim 10 wherein said aryl siloxane units are diphenyl siloxane units.

14. The intraocular lens of claim 11 wherein said alkyl siloxane units have the formula $R_6 R_7$-SiO wherein $R_6$ and $R_7$ are independently selected from methyl or ethyl.

15. The intraocular lens of claim 10 wherein said polymer includes end blockers containing siloxane units of the formula $R_1 R_2 R_3$-SiO$_{0.5}$ wherein $R_1$ and $R_2$ are independently selected from alkyl, aryl, substituted alkyl and substituted aryl, and $R_3$ is alkenyl.

16. The intraocular lens of claim 10 wherein said lens body has an optical refractive index of at least 1.459.

17. The intraocular lens of claim 10 wherein said lens body has physical properties sufficient to enable said lens to be placed in a folded shape for insertion into a human eye through a small incision, said physical properties including: a Shore Type A durometer value of at least 35, a tensile strength of at least 500 psi and a tear strength of at least 20 pli.

18. The intraocular lens of claim 15 wherein $R_1$ and $R_2$ are methyl and $R_3$ is vinyl.

19. An intraocular lens suitable for surgical implantation into a human eye comprising an appropriately sized lens body capable of being folded, and made of an optically clear elastomeric material comprising:

a cross-linked silicone polymer containing approximately 12 to 18 mol percent of aryl siloxane units; and silica reinforcer present in an amount effective to reinforce said polymer, said lens body having an optical refractive index of at least 1.44 and an effective combination of hardness, elongation, tensile strength and tear strength to enable said lens body to be placed in a folded shape for insertion into a human eye and to unfold into an unfolded shape after said insertion, said lens body having a Shore Type A durometer value of at least 35, a tensile strength of at least 500 psi, and 150 percent minimum elongation and a tear strength of at least 20 pli.

* * * * *